United States Patent
Kita et al.

(10) Patent No.: US 10,393,763 B2
(45) Date of Patent: Aug. 27, 2019

(54) ODOR DISCRIMINATING APPARATUS

(75) Inventors: Junichi Kita, Kyoto (JP); Motoo Kinoshita, Kyoto (JP); Hisamitsu Akamaru, Kyoto (JP); Masayuki Okada, Kyoto (JP)

(73) Assignee: Shimadzu Co., Kyoto (JP)

( * ) Notice: Subject to any disclaimer, the term of this patent is extended or adjusted under 35 U.S.C. 154(b) by 1157 days.

(21) Appl. No.: 13/806,833

(22) PCT Filed: Jul. 6, 2010

(86) PCT No.: PCT/JP2010/061486
§ 371 (c)(1),
(2), (4) Date: Mar. 14, 2013

(87) PCT Pub. No.: WO2012/004861
PCT Pub. Date: Jan. 12, 2012

(65) Prior Publication Data
US 2013/0179089 A1 Jul. 11, 2013

(51) Int. Cl.
*G01N 35/00* (2006.01)
*G01N 1/22* (2006.01)
(Continued)

(52) U.S. Cl.
CPC ......... *G01N 35/00584* (2013.01); *G01N 1/22* (2013.01); *G01N 33/0031* (2013.01); *G01N 1/38* (2013.01); *G01N 1/405* (2013.01)

(58) Field of Classification Search
CPC ........... G01N 1/22; G01N 1/38; G01N 1/405; G01N 33/0031; G01N 35/00584
See application file for complete search history.

(56) References Cited

U.S. PATENT DOCUMENTS

2002/0002857 A1* 1/2002 Aoyama et al. ............. 73/23.34
2003/0172717 A1* 9/2003 Kita et al. .................... 73/23.34
(Continued)

FOREIGN PATENT DOCUMENTS

| JP | 10-090207 | 4/1998 |
| JP | 2003-315298 | 11/2003 |
| JP | 2010-107474 | 5/2010 |

OTHER PUBLICATIONS

English Translation of Nakamura et al., JP 10090207 A, Apr. 10, 1998.*

(Continued)

*Primary Examiner* — Kyle R Quigley
(74) *Attorney, Agent, or Firm* — Chris Mizumoto

(57) ABSTRACT

An odor discriminating apparatus includes: a measurement chamber including multiple pieces of odor sensors; a gas introducer for introducing a sample gas into the measurement chamber; concentration adjuster for diluting or condensing the sample gas before introducing the sample gas into the measurement chamber; a vector length computation unit for plotting, in a multidimensional space formed by axes corresponding to detection signals generated by each piece of odor sensors, a measurement point representing a measurement result of the sample gas and for computing a vector length of an odor vector directed from an origin of the multidimensional space to the measurement point; and a controller for feedback-controlling the concentration adjuster so that the vector length computed by the vector length computation unit reaches a predetermined target value.

2 Claims, 4 Drawing Sheets

(51) Int. Cl.
*G01N 33/00* (2006.01)
*G01N 1/38* (2006.01)
*G01N 1/40* (2006.01)

(56) References Cited

U.S. PATENT DOCUMENTS

2005/0252275 A1\* 11/2005 Kita et al. ................. 73/23.34
2013/0244336 A1\* 9/2013 Mayer ................ G01N 33/0004
436/147

OTHER PUBLICATIONS

International Preliminary Report on Patentability and its English translation.

\* cited by examiner

ODOR DISCRIMINATING APPARATUS

TECHNICAL FIELD

The present invention relates to an odor discriminating apparatus for evaluating the odors, such as smells and scents, of various kinds of substances.

BACKGROUND ART

The discrimination or evaluation of an odor is generally performed based on the olfactory sense of a human being. This requires consideration of the fact that there are personal differences among those (a panel) who actually smell the odor and that their olfactory senses vary according to their physical condition of the day. Therefore, in order to obtain an accurate and objective result, it is necessary to ensure that the panel contains an adequate number of persons and to pay proper attention to the atmosphere of the testing location and other factors, which requires a substantial amount of time and labor. Additionally, even if such matters are given attention, it is difficult to constantly obtain a definitive determination at a certain standard because of the fact that the olfactory sense of a human being tends to adapt to an odor.

To solve such problems, odor discriminating apparatuses have been developed that use odor sensors which react to odorous substances. These odor discriminating apparatuses obtain detection signals from plural odor sensors having different characteristics and process the detection signals employing a multivariate analysis, such as cluster analysis or principal component analysis, or non-linear analysis using a neural network. As a result, the odor discriminating apparatuses can determine the distances between the odors of plural samples (i.e. whether or not these odors belong to the same or similar categories).

Another recently developed odor discriminating apparatus evaluates the odor of a sample gas in terms of both the quality and strength, and respectively quantifies them (refer to Patent Document 1, for example). An example of evaluating the difference of the quality of odors among a plurality of samples using such an odor discriminating apparatus is described with reference to FIG. 6. The odor of one sample is set as a reference odor, and that of another sample as a subject odor. In a multidimensional odor space formed by the detection signals from a plurality of odor sensors having different characteristics, the measurement point Q which represents the measurement result of the reference odor, and the measurement point P which represents the measurement result of the subject odor, are plotted. For easer understanding, the odor space in FIG. 6 is a two-dimensional odor space formed by the detection signals from two odors sensors. The reference odor vector S1, directed from the origin to the measurement point Q of the reference odor, and the subject odor vector Sx, directed from the origin to the measurement point P of the subject odor, are determined. Then, the angle $\theta$ between the two vectors is obtained. Since each vector shows a direction specific to its odor, if the angle $\theta$ is small, the two odors belong to the same or similar categories. Conversely, if the angle $\theta$ is large, they belong to different categories.

Sensors using oxide semiconductors, which are generally employed in an odor discriminating apparatus, show a non-linear response to the change in the concentration. Therefore, such non-linearity should be taken into account when actually analyzing measurement data. That is, if the relationship between the concentration of an odor component and its detection signal is linear in each odor sensor, the odor vectors have a linear shape as shown in FIG. 6. However, in sensors using metal oxide semiconductors, the relationship between the concentration of an odor component and its detection signal is not linear, and the non-linearity is different for each sensor. Hence, the odor vectors have a curved shape. That is, when an odor having the same quality but having different concentrations are measured, the locus of the measurement points will have a curved shape. Regarding this question, when the difference in the quality of odors between different samples is to be evaluated, conventionally, the influence of the concentration is canceled as follows. As shown in FIG. 7, the concentration of a reference odor is incrementally changed and the data is measured at, for example, three points. Then, a curve along the measured points a1, a1, and a3 is created. This curve is called a reference odor curve H1. The similarity is determined as follows. First, a line perpendicular to the reference odor curve H1 is drawn from the measurement point P of a sample measured. The foot of the perpendicular line on the reference odor curve is denoted as K. Then, the length of the perpendicular line, i.e. the distance dmin between the measurement point P and the point K, is computed, and the length L of the reference odor curve H1 from the origin to the point K is also computed. Subsequently, the angle $\theta$ is computed using the following equation:

$$\tan \theta = d\mathrm{min}/L.$$

Based on the value of the angle $\theta$, the similarity of the odor qualities is computed.

BACKGROUND ART DOCUMENT

Patent Document

[Patent Document 1] JP-A 2003-315298

DISCLOSURE OF THE INVENTION

Problem to be Solved by the Invention

In the aforementioned method, an error inevitably arises because the relationship of the sensor outputs and the concentrations, which is substantially non-linear, is approximated only by three points. Such error causes a difference between the result of the above method and that of an organoleptic evaluation, especially when discriminating the slight difference in odor quality between similar samples, such as between teas or between coffees.

The present invention has been achieved to solve the aforementioned problem, and the objective thereof is to provide an odor discriminating apparatus capable of accurately evaluating a slight change in an odor quality or a slight difference of odor qualities.

Means for Solving the Problem

To solve the aforementioned problem, the present invention provides an odor discriminating apparatus, including:
a) a measurement chamber including m pieces of odor sensors having different responsive characteristics where m is an integer greater than one;
b) a gas introducer for introducing a sample gas into the measurement chamber;
c) a concentration adjuster for diluting or condensing the sample gas before introducing the sample gas into the measurement chamber;

d) a vector length computation unit for plotting, in a m-dimensional space formed by axes each corresponding to a detection signal generated by each of the m pieces of odor sensors, a measurement point representing a measurement result of the sample gas and for computing a vector length of an odor vector starting from an origin of the m-dimensional space and ending at the measurement point; and e) a controller for feedback-controlling the concentration adjuster so that the vector length computed by the vector length computation unit reaches a predetermined target value.

The vector length of an odor vector corresponds to the intensity of the odor, i.e. the concentration of odor molecules in the sample gas. Therefore, by performing an odor measurement after the sample gas has been diluted or condensed so that the vector length is always constant, the measurement can be performed under conditions where the odor molecules have approximately the same concentration in respective sample gases. This reduces the influence of different concentrations among the sample gases, and enables an accurate evaluation of the difference of their odor qualities.

In the odor discriminating apparatus according to the present invention, it is preferable to set the target value at a length at which the measurement result is least affected by the non-linearity of outputs of the m pieces of odor sensors.

This suppresses the influence of the non-linearity of the sensor outputs, and enables a more accurate evaluation of the difference of the odor qualities of multiple sample gases.

In the odor discriminating apparatus according to the present invention, it is preferable that the controller sets an allowance range across the target value and controls the gas introducer and the concentration adjuster so as to measure the odor of one sample gas at least two points in which the vector lengths of the odor vectors are shorter and longer than the target value within the allowance range; and the odor discriminating apparatus further includes:

f) a measurement result computation unit for computing a measurement result at which the vector length is equal to the target value using a first measurement result and a second measurement result, the first measurement result being a result of measurement when the vector length is shorter than the target value within the allowance range and the second measurement result being a result of measurement when the vector length is longer than the target value within the allowance range, and for setting the computed measurement result as the measurement result of the sample gas.

With this configuration, measurements are performed above and below the target value, and the measurement result in which the vector length corresponds to the target value is obtained by means of a computation. Therefore, in measuring a sample gas, the vector length does not have to bring equal to the target value. This makes it possible to easily obtain the measurement result of each sample gas in a short time.

With this configuration, it is more preferable that, when the vector length of the odor vector is shorter than the target value within the allowance range, the condition of dilution or condensation by the concentration adjuster is fixed to a value at this point in time, measurements are repeated under the same condition, and the measurement value when the direction of the odor vectors is settled is set as the first measurement value; and when the vector length of the odor vector is longer than the target value within the allowance range, the condition of dilution or condensation by the concentration adjuster is fixed to a value at this point in time, measurements are repeated under the same condition, and the measurement value when the direction of the odor vectors is settled is set as the second measurement value.

This reduces the influence of the memory effect of odor sensors to the measurement results, and enables a more accurate odor measurement.

Effects of the Invention

As above described, in the odor discriminating apparatus according to the present invention, a sample gas is diluted or condensed so that the length of the odor vector obtained by measuring the sample gas is constant. This reduces the influence caused by the difference in concentration between the sample gases on the evaluation of their odor quality, thereby enabling an accurate evaluation of slight changes and slight differences in odor quality.

In the case where the target value of the vector length is set at a length at which the measurement result is least affected by the non-linearity of the outputs of the m pieces of odor sensors, it is possible to measure a sample gas at an optimum concentration at which the non-linearity of the sensor outputs has little influence on the measurement result. This enables a more accurate evaluation of the difference in the odor quality among a plurality of sample gases.

BEST MODES FOR CARRYING OUT THE INVENTION

Figure 1:
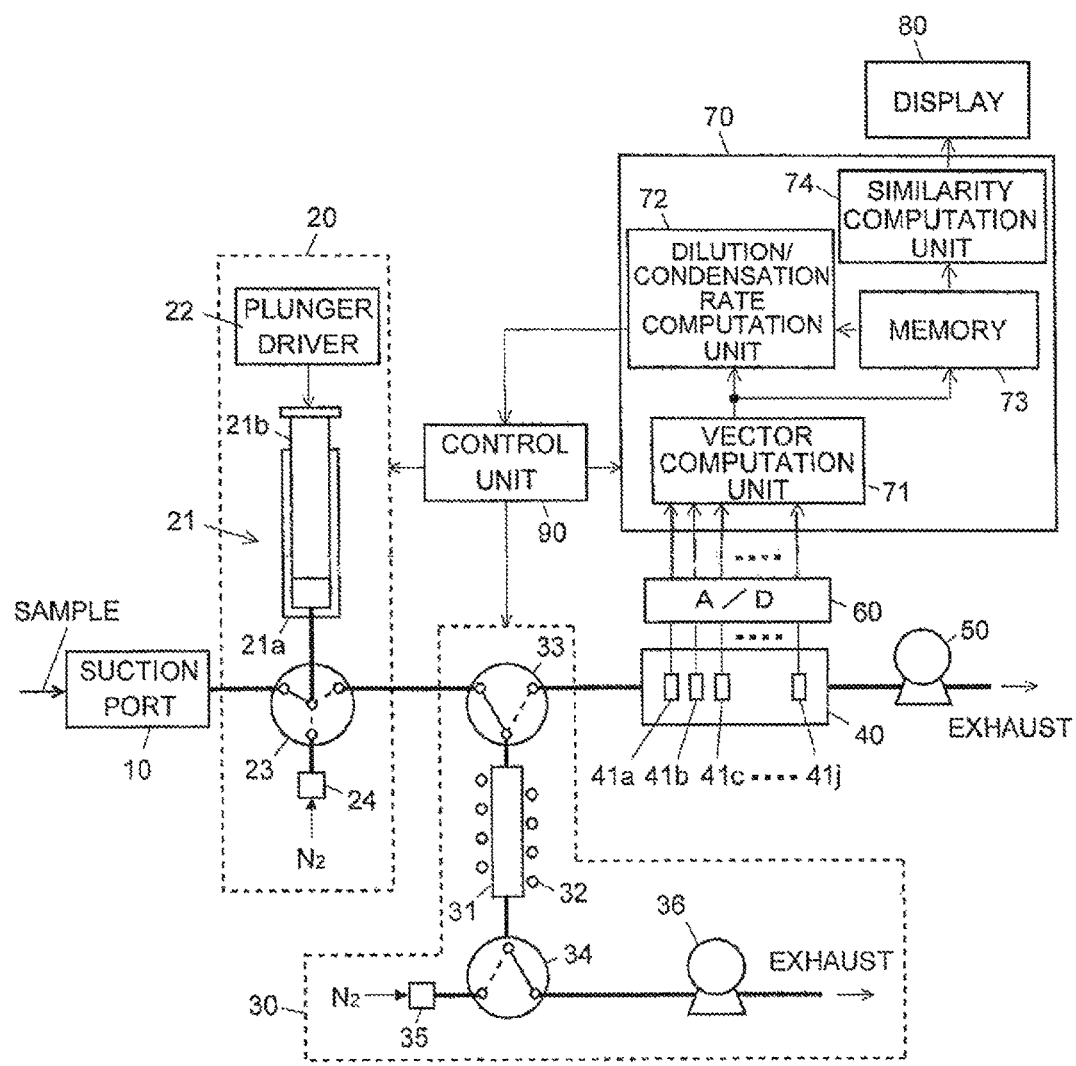
FIG. 1 is an entire configuration diagram of an odor discriminating apparatus according to an embodiment of the present invention.

Hereinafter, an odor discriminating apparatus which is an embodiment of the present invention will be described with reference to the figures. FIG. 1 is a schematic configuration diagram of the odor discriminating apparatus of the present embodiment.

The present odor discriminating apparatus includes the following elements: a suction port 10 for sucking a gas sample; a dilution unit 20 for diluting the sucked gas; a condensation unit 30 for condensing the sucked sample gas; a sensor cell 40 with plural (ten in the case of FIG. 1) odor sensors 41*a* through 41*j* for measuring a sample gas containing various odor components, each sensor having a different responsive characteristic; a pump 50 for drawing the gas sample into the sensor cell 40; an analogue-to-digital (A/D) converter 60 for converting the detection signals of the odor sensors 41*a* through 41*j* into digital signals; a signal processor 70 for analyzing the digitized detection data; a display 80 for displaying the analysis results on a screen; and a control unit 90 for controlling the overall operation of the apparatus.

In the present odor discriminating apparatus, the sensor cell 40 corresponds to the measurement chamber in the present invention, and the pump 50 to the gas introducer. Both the dilution unit 20 and the condensation unit 30 correspond to the concentration adjuster in the present invention, the signal processor 70 to the vector length computation unit and the measurement result computation unit, and the control unit 90 to the controller.

The odor sensors 41a through 41j are, for example, sensors using metal oxide semiconductors whose resistances vary depending on the kind and concentration of odor components. Other examples of the odor sensors include: a sensor using conducting polymers; and a sensor using quartz resonators or SAW (surface acoustic wave) devices coated with a gas absorption film. The signal processor 70 and the control unit 90 are constructed using mainly a personal computer. Running a program on the personal computer enables the computer to perform the functions of a vector computation unit 71, a dilution/condensation rate computation unit 72, a memory 73, and a similarity computation unit 74, which will be described later.

The dilution unit 20 includes a syringe 21 and a first valve (4-port 3-position valve) 23 for connecting the suction/discharge port of the syringe 21 to any one of the suction port 10, a nitrogen gas supply port 24, and a second valve 33. The syringe 21 includes a cylinder 21a with a predetermined volume and a plunger 21b inserted into the cylinder 21a. The plunger 21b can be reciprocated in the cylinder 21a. The plunger 21b is driven by a plunger driver 22 which includes a drive source such as a motor. In the dilution unit 20, the sample gas flowing from the suction port 10 to the sensor cell 40 can be diluted with a nitrogen gas by performing suction/discharge operations with the syringe 21 while selecting the connection of the first valve 23.

More specifically, while the syringe 21 is connected to the suction port 10, a predetermined amount of sample gas is sucked from the suction port 10 into the syringe 21, where the sucked gas is stored. Then, the first valve 23 is operated so as to connect the syringe 21 to the nitrogen gas supply port 24, and a predetermined amount of nitrogen gas is sucked from the nitrogen gas supply port 24 into the syringe 21. After that, the first valve 23 is operated so as to connect the syringe 21 to the second valve 33. The sample gas and the nitrogen gas which have been mixed in the cylinder 21a are discharged therefrom and introduced into the sensor cell 40 through the second valve 33. The dilution rate of the sample gas is determined by the amount of sample gas and nitrogen gas sucked into the syringe 21. Therefore, the dilution rate of the sample gas which is introduced to the sensor cell 40 can be adjusted by the appropriate setting of the suction amount of sample gas and nitrogen gas by means of the control unit 90, which accordingly controls the driving amount of the plunger 21b by the plunger driver 22.

The condensation unit 30 includes: a collection pipe 31 equipped with a heater 32; the second valve (3-port-3-position valve) 33 for selectively connecting any two of the gas passage which is connected to one end of the collection pipe 31, the first valve 23, and the sensor cell 40; and a third valve (3-port 2-position valve) 34 for connecting the gas passage which is connected to the other end of the collection pipe 31 to either a nitrogen gas supply port 35 or a pump 36. The collection pipe 31 is filled with an appropriate adsorbent, such as a carbon adsorbent, depending on the components of the sample to be measured.

In order to condense the sample gas by the condensation unit 30, initially, the second valve 33 and the third valve 34 are changed to the state shown with solid lines in FIG. 1, and then the pump 36 is operated. As a consequence, the gas supplied through the first valve 23 passes through the collection pipe 31 and is ejected therefrom. Various components contained in the gas are adsorbed by the adsorbent in the collection pipe 31. Subsequently, both the first valve 23 and the second valve 33 are changed to the state shown with dashed lines in FIG. 1. Then, a dried nitrogen gas which is supplied to the nitrogen gas supply port 35 at a high gas pressure (at least higher than the atmospheric pressure) flows to the sensor cell 40 through the collection pipe 31. While in this state, the temperature of the collection pipe 31 is rapidly increased by turning on the heater 32. Consequently, the odor components adsorbed in the adsorbent are desorbed from the adsorbent, and are introduced into the sensor cell 40 by the flow of the dried nitrogen gas.

In the condensation unit 30, the condensation rate of the sample gas is determined by the total flow amount of the sample gas which passes through the collection pipe 31 when the components are adsorbed and the total flow amount of the carrier gas which passes through the collection pipe 31 when the components are desorbed, as long as the adsorption is not saturated. Therefore, the concentration rate of the sample gas introduced into the sensor cell 40 can be adjusted by the appropriate setting of the total flow amount of the sample gas and that of the carrier gas by means of the control unit 90, which accordingly operates the second valve 33, the third valve 34, and the pump 36. The collection pipe 31 can be used for removing water or removing interfering components such as alcohol from the sample gas. However, the explanation thereof is omitted because it does not directly relate to the present invention.

The measurement principle of the odor discriminating apparatus having the aforementioned configuration is described hereinafter. In the present odor discriminating apparatus, when a sample gas to be measured is introduced into the sensor cell 40, the components contained in the sample gas come into contact with the odor sensors 41a through 41j. The odor sensors 41a through 41j generate different detection signals in parallel. The detection signals are sampled and digitized by the A/D converter 60, and provided to the signal processor 70. Since the signal processor 70 receives one piece of detection data from each odor sensor for one sample gas, a total of ten pieces of detection data DS1 through DS10 are obtained as a result of a measurement of a sample gas. Since the ten odor sensors 41a through 41j have different responsive characteristics, a ten-dimensional odor space can be formed by ten axes corresponding to the ten different detection signals generated by the ten odor sensors 41a through 41j. The origin of this odor space represents the state where all the detection signals from the odor sensors 41a through 41j are zero.

In the aforementioned odor space, the ten pieces of detection data can be plotted as one measurement point (DS1, DS2, DS3, DS4, DS5, DS6, DS7, DS8, DS9, and DS10). The length of an odor vector starting from the origin of the odor space and ending at the measurement point corresponds to the "odor intensity" (i.e. the concentration of the odor components contained in the sample gas), and the direction of the odor vector corresponds to the "odor quality." That is, if the direction of one odor vector obtained by a measurement of a sample gas is similar to that of another odor vector obtained by a measurement of another sample gas, these odors belong to the same or similar categories. If the directions of the vectors are significantly different, these odors belong to different categories. Then, the angle θ formed by two vectors is used as an index to determine the directional similarity of the two vectors. The similarity of the "odor qualities" can be determined using the angle θ. For example, the similarity when two odor vectors overlap each other (i.e. when they have exactly the same direction; θ=0) is defined as 100%, and the similarity when the angle θ is equal to or more than a predetermined value α is defined as 0%. When the angle θ is between 0 and α, the similarity is defined depending on the angle θ.

In the case where the detection signal level of the odor sensors for the concentration of the sample gas (the concentration of the odor components) is almost linear, the odor vectors for the same or similar kinds of odor are directed in the same direction irrespective of the concentration. Therefore, irrespective of their concentration, the angle θ formed by the two odor vectors is constant, which enables an accurate determination of the difference in the odor quality among a plurality of sample gases. However, in the case where the sensor output for the concentration of odor components is nonlinear, as with sensors using metal oxide semiconductors, which are generally used in an odor discriminating apparatus, the directions of the odor vectors differ, even though the odors belong to the same or similar categories. In this case, it is difficult to accurately determine the difference in the odor quality among a plurality of sample gases.

Figure 2:
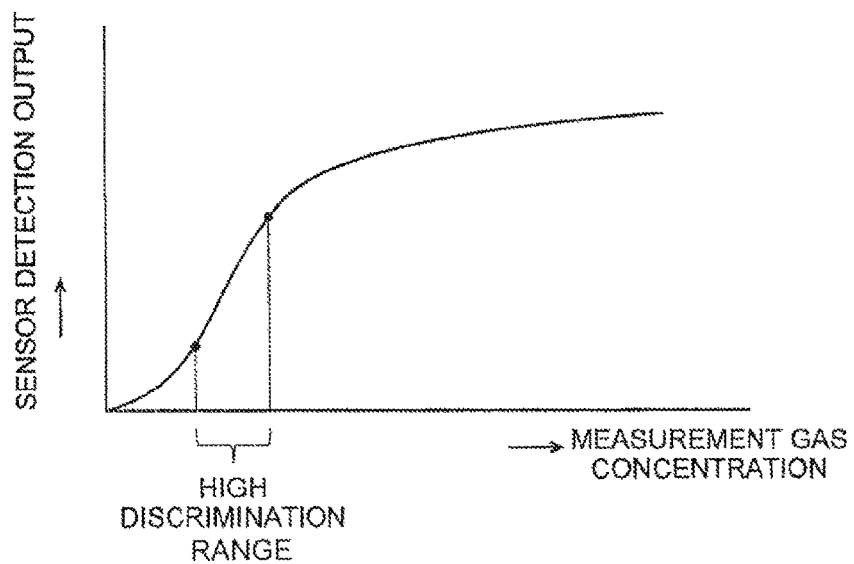
FIG. 2 shows the concentration dependency of the detection output of an odor sensor.

FIG. 2 shows an example of a response curve to the gas concentration of a metal-oxide semiconductor. The abscissa of FIG. 2 logarithmically indicates the gas concentration (the concentration of the odor molecules) and the ordinate logarithmically indicates the detection signal of the sensor. As shown in FIG. 2, as a whole, the sensor output for the gas concentration is nonlinear. However, in a certain concentration range, the relationship between the logarithm of the gas concentration and that of the sensor output is substantially linear. In addition, in a low concentration range and in a high concentration range, the sensor output does not increase in accordance with an increase in the gas concentration. In contrast, in the aforementioned concentration range, the sensor output significantly changes as the gas concentration changes. Therefore, if sample gases can be measured in this concentration range, the difference in odor quality is accurately determined. Hereinafter, this concentration range is referred to as "high discrimination range."

In the odor discriminating apparatus according to the present invention, when measuring a sample gas, the dilution unit 20 and the condensation unit 30 are feedback-controlled based on the output values from the odor sensors 41a through 41j in order for the concentration of the sample gas introduced into the sensor cell 40 to be appropriately maintained. In particular, by means of the vector computation unit 71, the detection signals DS1 through DS10 obtained from the ten odor sensors 41a through 41j are plotted as one measurement point in the aforementioned odor space, an odor vector starting from the origin and ending at the measurement point is generated, and the length of the odor vector is obtained. Then, the dilution rate in the dilution unit 20 or the condensation rate in the condensation unit 30 is controlled so that the length is a predetermined value (which is hereinafter referred to as a "target value A").

The target value A may be determined as follows, for example. First, a provisional target value A' is suitably set. While dilution unit 20 and/or the condensation unit 30 is feedback-controlled so that the length of the odor vector reaches the provisional target value A', a plurality (nine in this example) of standard gases are measured. The angles between the odor vectors of the standard gases are measured by the vector computation unit 71. Then, the lengths of the odor vectors of the nine kinds of standard gases are changed so as to be across the provisional target value A'. That is, the nine kinds of standard gases are measured when each of the odor vectors is shorter than the provisional target value A' by a predetermined length by means of feedback-control of the dilution unit 20 and/or the condensation unit 30, and when each of the odor vectors is longer than the provisional target value A' by a predetermined length by means of feedback-control of the dilution unit 20 and/or the condensation unit 30. Then the angles between the vectors of the standard gases are determined in each case. Subsequently, the angle difference between the vectors across the provisional target value A' is computed. As previously described, the length of an odor vector corresponds to the intensity of the odor of the sample gas (i.e. the concentration of the gas). If the gas concentration is in the high discrimination range of each sensor, there is almost no change in the angles between the vectors even if there is a slight change in the lengths of the vectors (i.e. when the gas concentration changes a little). In contrast, if the gas concentration is out of the high discrimination range, a slight change in the length of the vectors causes significant changes in the angles between the vectors. Therefore, the aforementioned measurement is repeated while changing the provisional target value A' at fixed intervals. The provisional target value A' at which the difference of the angles between the vectors is smallest is determined to be an ultimate target value A. The target value A determined in this manner is the length of the vectors at which the non-linearity of the outputs of odor sensors least affects the measurement result.

Although each sensor responds to almost any kind of odor molecules, every sensor has a stronger responsiveness to some kinds of odor molecules and a weaker responsiveness to other kinds of molecules. Such a difference in the responsiveness enables a determination of the difference in odor qualities. However, in the case where there is an excessive difference of responsiveness among the sensors for the same kind of gas, contrarily, the difference in the odor quality might not be accurately discriminated. Given this factor, in the odor discriminating apparatus of the present invention, it is preferable to perform a standardization for uniforming the dynamic ranges of the sensors.

In particular, for example, measurements are performed using the ten sensors while changing the concentrations of a plurality (nine in this embodiment) of standard gases. Then, a respone curve representing the relationship between the gas concentration and the sensor output is created for each sensor. Then, the average value (AVEH) of the data at the highest points in the high discrimination ranges on the 90 response curves (for 9 kinds of gases×10 sensors) is obtained from the measurements. Similarly, the average value (AVEL) of the data at the lowest points in their high discrimination ranges is obtained. Next, for each of the ten sensors, the average values of the data at the highest point and the average values of the data at the lowest point in the high discrimination range are obtained for nine response curves of the standard gas. Then, the output signal of each sensor is corrected so that these average values become AVEH and AVEL.

The standard gas may be appropriately selected depending on the odor to be measured. For example, in a versatile bad odor measurement apparatus, gases containing odor components of aromatic system (e.g. xylene), hydrocarbon system (e.g. butane), ester system (e.g. ethyl acetate) or the like may be used as standard gases for benign odors, and gases containing odor components of amine system (e.g. tributylamine), aldehyde system (e.g. pentylaldehyde), sulfur system (e.g. methyl mercaptan), organic acid system (e.g. butyric acid), ammonia, hydrogen sulfide, or the like may be used as standard gases for unfavorable odors.

The procedure for measuring the odor of a sample gas a and that of a sample gas b and obtaining the difference (similarity) of their odor quality with the aforementioned odor discriminating apparatus is described hereinafter. The target value A of the vector length is determined in advance by the aforementioned method and memorized in the memory 73.

First, the sample gas a is introduced into the sensor cell 40 from the suction port 10. For example, a bag containing the sample gas a is connected to the suction port 10, and the pump 50 is energized. The sample gas a is sucked by the syringe 21, and the first valve 23 is operated to connect the syringe 21 with the second valve 33, so that the sample gas a held within the syringe 21 is discharged. As a result, the sample gas a is drawn into the sensor cell 40 without being diluted by a nitrogen gas.

When the components contained in the sample gas a introduced into the sensor cell 40 come into contact with the odor sensors 41a through 41j, different detection signals are provided from the odor sensors 41a through 41j. The detection signals are sent to the signal processor 70 through the A/D converter 60. Then, the vector computation unit 71 creates the odor vector of the sample gas a from the detection signals of the sensors, and computes the length of the vector. After that, the dilution/condensation rate computation unit 73 compares the vector length with the target value A read out from the memory 73, computes the dilution rate or condensation rate of the sample gas a required to make the length of the odor vector of the sample gas a be the target value A, and sends it to the control unit 90.

The control unit 90 controls the dilution unit 20 or the condensation unit 30 so as to attain the dilution rate or the condensation rate. That is, in the case where the sample gas a is required to be diluted, the sample gas a is sucked by the syringe 21, mixed with a nitrogen gas by the aforementioned procedure in the dilution unit 20, and then sent to the sensor cell 40. In the case where the sample gas a is required to be condensed, the sample gas a is sucked by the syringe 21, and sent from the syringe 21 to the collection pipe 31 of the condensation unit 30. Then, the sample gas a is condensed by the aforementioned procedure and sent to the sensor cell 40. The result of the measurement in the sensor cell 40 is analyzed again in the signal processor 70. Then, the dilution rate or the condensation rate is changed so that the length of the odor vector becomes closer to the target value A, and the odor measurement of the sample gas a is performed.

As described above, the sample gas is repeatedly measured while changing the dilution rate or condensation rate. When the length of the vector reaches the target value A, the odor vector at this point in time is memorized in the memory 73 as the measurement result of the sample gas a. Then, the measurement of the sample gas a is finished.

In an actual measurement, it is difficult to make the length of the odor vector perfectly equal to the target value A. In addition, odor molecules in the sample gas adhere to the odor sensors 41a through 41j, which influences the values of the subsequent measurement (a so-called memory effect). In particular, the direction of an odor vector is more easily influenced by the memory effect compared to the length of the odor vector. In light of these factors, the concentration adjustment and the measurement of the sample gas may be preferably performed as follows.

Figure 3:
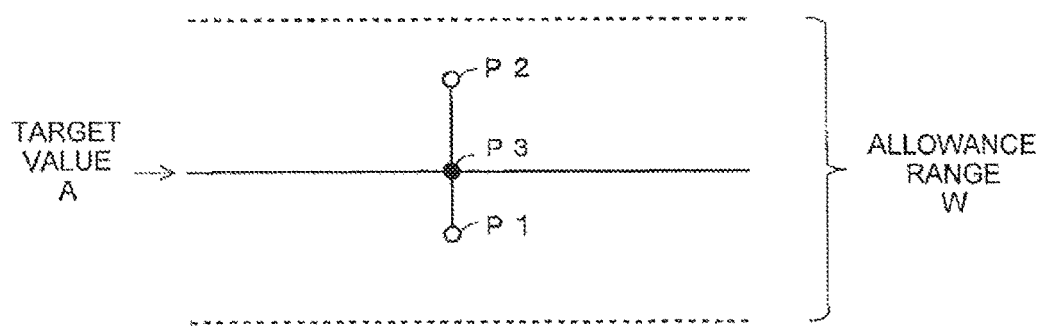
FIG. 3 is a diagram for explaining the procedure of an odor measurement.

As shown in FIG. 3, an allowance range W having a predetermined width across a predetermined value A is set in advance. Then, as previously described, the sample gas a is repeatedly measured while changing the dilution rate or the condensation rate.

When the vector length is within the allowance range W (P1 in FIG. 3), the dilution rate in the dilution unit 20 or the condensation rate in the condensation unit 30 is fixed to the current value. Then, the measurement under the same conditions is repeated until the direction of the odor vector is settled. In particular, the angle difference between the odor vector obtained from the latest measurement and that obtained from the previous measurement is computed, and a measurement under the same conditions is repeated until the angle difference is smaller than a predefined allowable tolerance. When the direction of the odor vector is settled (that is, when the angle difference is smaller than the allowable tolerance), the odor vector at this point in time is memorized as a provisional odor vector Sa1 in the memory 73.

Subsequently, the vector length is changed and the same measurement is performed. In this measurement, when the length of the provisional odor vector Sa1 is shorter than the target value A, the measurement is repeated while the concentration of the sample gas is gradually increased so that the length of the odor vector becomes longer than the target value A. When the odor vector is longer than the target value A and is not above the allowance range (P2 in FIG. 3), the dilution rate or the condensation rate is fixed to the value at this point in time. Then, as before, a measurement under the same conditions is repeated. When the direction of the odor vector is settled, the odor vector at this point in time is memorized as a provisional odor vector Sa2 in the memory 73.

Conversely, when the length of the provisional odor vector Sa1 is longer than the target value A, the measurement is repeated while the concentration of the sample gas is gradually decreased so that the length of the odor vector becomes shorter than the target value A. When the odor vector is longer than the target value A and is not below the allowance range, the dilution rate or the condensation rate is fixed to the value at this point in time. Then, as before, a measurement under the same conditions is repeated. When the direction of the odor vector is settled, the odor vector at this point in time is memorized as a provisional odor vector Sa2 in the memory 73.

After the provisional odor vector Sa1 and the provisional odor vector Sa2 are obtained in the aforementioned manner, the vector computation unit 71 computes the vector length of the odor vector that corresponds to the target value A (P3 in FIG. 3) based on the vectors Sa1 and Sa2. This odor vector is memorized as the odor vector Sa of the sample gas a in the memory 73.

After that, the same measurement is performed for the sample gas b to obtain the odor vector with its vector length corresponding to the target value A. This odor vector is memorized as the odor vector Sb of the sample gas b in the memory 73.

After the odor measurements of the sample gases a and b are finished, as described above, the similarity computation unit 74 reads out the odor vector Sa of the sample gas a and the odor vector Sb of the sample gas b, which are memorized in the memory 73. Then, the similarity computation unit 74 obtains the angle $\theta$ between the two vectors, and computes their similarity based on the angle $\theta$.

The method for evaluating the difference in odor quality between the sample gases a and b based on their measurement results is not limited to the aforementioned one. For example, the method described in JP-A 2007-248377 may be used. The method described in this patent document (this method is referred to as an "odor variant mapping method" hereinafter) is as follows. Calibration reference odors (which will be hereinafter is referred to as a "reference variant odors") are prepared by adding a different odor of a different concentration to a central odor, and the calibration reference odor is measured so as to create another reference axis by means of the added odor in a multidimensional space formed by odor sensors. The information on the odor to be evaluated is created based on the positional relationship between the reference axes, which are created for each of the different added odors, and measurement points of the odor to be evaluated. In this evaluation method, an organoleptic expression corresponding to a human organoleptic evaluation, such as a "rotten fruit odor," is determined for each of a plurality of reference variant odors which are composed of the same central odor and a different added odor. The use of such an expression enables a more comprehensible description of the differences of the quality and changes of odor.

EXAMPLE

Figure 4:
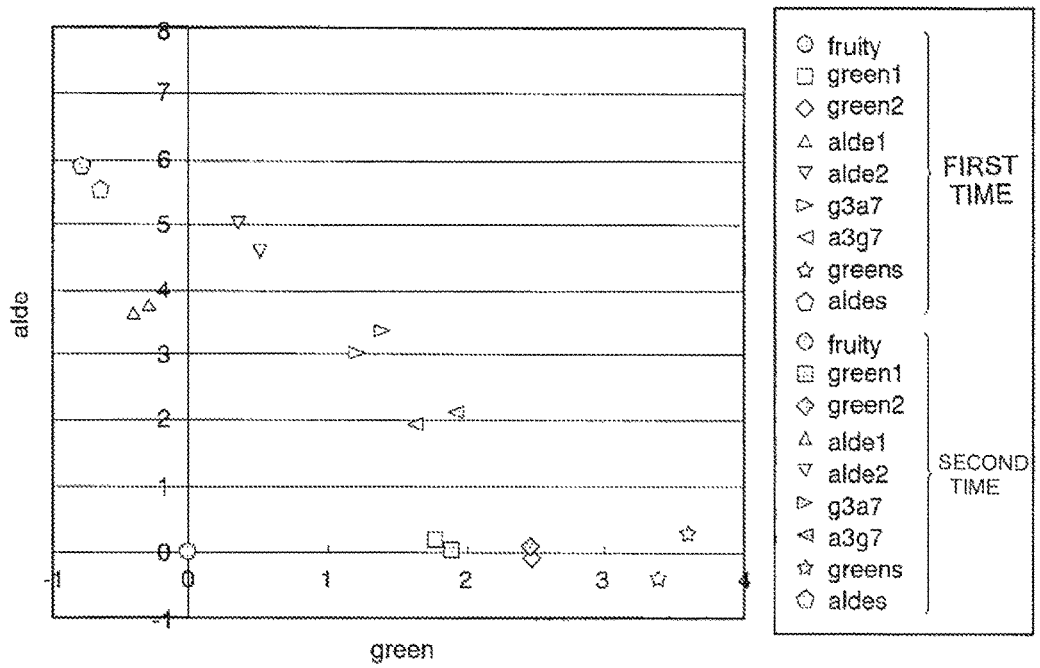
FIG. 4 shows an example of a measurement result obtained by the odor discriminating apparatus of the present invention.
Figure 5:
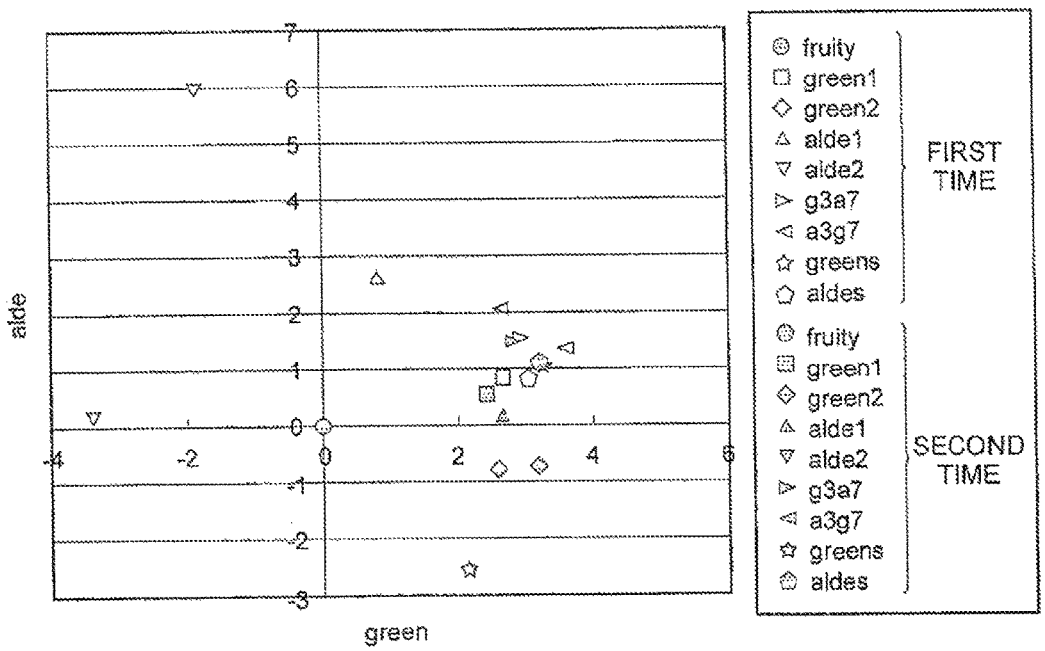
FIG. 5 shows an example of a measurement result obtained by a conventional odor discriminating apparatus.
Figure 6:
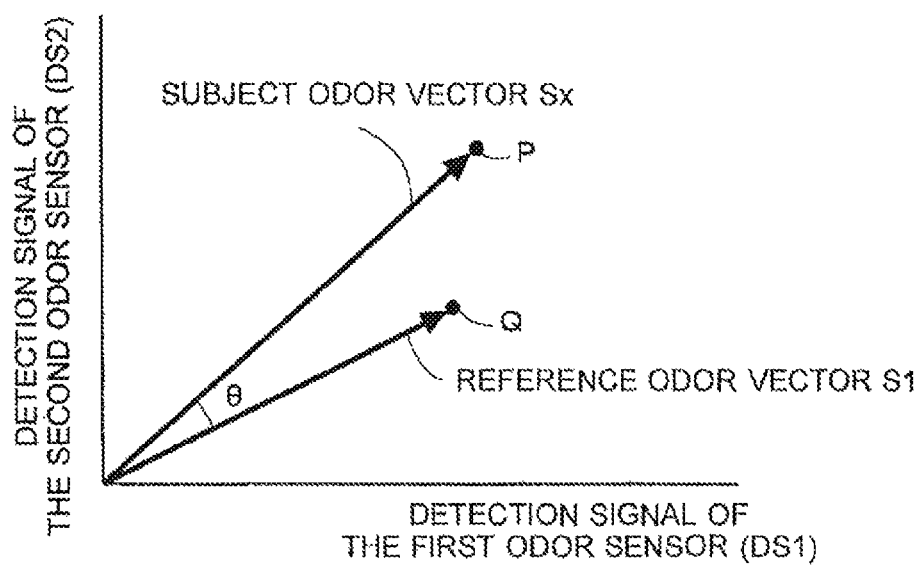
FIG. 6 is a diagram for explaining the measurement principle in a conventional odor discriminating apparatus.
Figure 7:
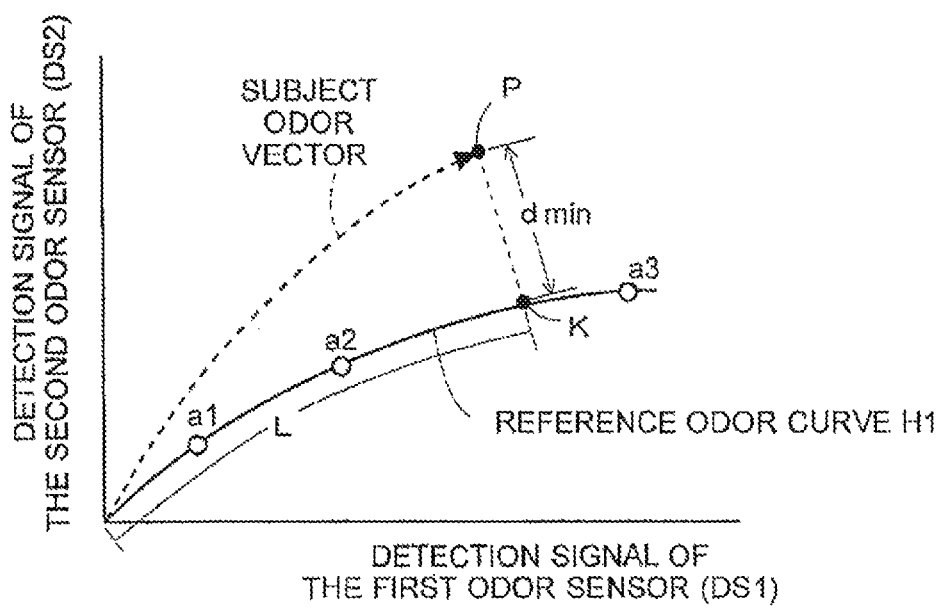
FIG. 7 is a diagram for explaining the measurement principle in a conventional odor discriminating apparatus.

FIGS. 4 and 5 show a result of an odor measurement for confirming the effects of the present invention. Each of these diagrams shows a result of two measurements of the odors of nine kinds of sample gases, as evaluated with the odor variant mapping method. FIG. 4 shows the result of measurements using the odor discriminating apparatus of the present invention, in which the dilution unit and the condensation unit were feedback-controlled so as to make the odor vectors always reach a target value. FIG. 5 shows a result of an odor measurement without uniforming the lengths of vectors as in the present invention. This falls into a conventional technology.

The legends "fruity," "greens," and "aldes" in FIGS. 4 and 5 represent the sample gases containing one of or a plurality of odors named "fruity," "green," and "aldehyde." The odors "green1" and "green2" were prepared by adding different concentrations of the odor "green" to the odor "fruity." The odors "alde1" and "alde2" were prepared by adding different concentrations of the odor "aldehyde" to the odor "fruity." The odor "g3a7" was prepared by adding a mixture of the odors "green" and "aldehyde" at a ratio of 3:7 to the odor "fruity." The odor "a3g7" was prepared by adding a mixture of the odors "aldehyde" and "green" at a ratio of 3:7 to the odor "fruity." In the graph of FIGS. 4 and 5, the origin represents the odor "fruity," the abscissa represents the reference axis corresponding to the odor "green," and the ordinate represents the reference axis corresponding to the odor "aldehyde."

As is clear from FIGS. 4 and 5, with the odor discriminating apparatus of the present invention, the measurement results of sample gases of the same kind are located closer to each other on the graph compared to the result obtained by a conventional method. At the same time, the measurement results of different sample gases are located at clearly discriminable positions on the graph. This shows that the odor discriminating apparatus of the present invention has an improved discrimination capacity than ever before.

EXPLANATION OF NUMERALS

10 . . . Suction Port
20 . . . Dilution Unit
21 . . . Syringe
22 . . . Plunger Driver
23 . . . First Valve
24, 35 . . . Nitrogen Gas Supply Port
30 . . . Condensation Unit
31 . . . Collection Pipe
32 . . . Heater
33 . . . Second Valve
34 . . . Third Valve
36, 50 . . . Pump
40 . . . Sensor Cell
41a through 41j . . . Odor Sensor
60 . . . A/D Converter
70 . . . Signal Processor
71 . . . Vector Computation Unit
72 . . . Dilution/Condensation Rate Computation Unit
73 . . . Memory
74 . . . Similarity Computation Unit
80 . . . Display
90 . . . Control Unit

The invention claimed is:

1. An odor discriminating apparatus comprising:
a) a measurement chamber including m pieces of odor sensors having different responsive characteristics where m is an integer greater than one;
b) a gas introducer for introducing a sample gas into the measurement chamber;
c) a concentration adjuster for diluting or condensing the sample gas before introducing the sample gas into the measurement chamber;
d) a vector length computation unit for plotting, in a m-dimensional space formed by axes each corresponding to a detection signal generated by each of the m pieces of odor sensors, a measurement point representing a measurement result of the sample gas and for computing a vector length of an odor vector starting from an origin of the m-dimensional space and ending at the measurement point; and
e) a controller for feedback-controlling the concentration adjuster so that the vector length computed by the vector length computation unit reaches a predetermined target value,
wherein: the controller sets an allowance range across the target value and controls the gas introducer and the concentration adjuster so as to measure an odor of one sample gas at least two points in which the vector lengths of the odor vectors are shorter and longer than the target value within the allowance range; and
the odor discriminating apparatus further comprises:
f) a measurement result computation unit for computing a measurement result at which the vector length is equal to the target value using a first measurement result and a second measurement result, the first measurement result being a result of measurement when the vector length is shorter than the target value within the allowance range and the second measurement result being a result of measurement when the vector length is longer than the target value within the allowance range, and for setting the computed measurement result as the measurement result of the sample gas.

2. An odor discriminating apparatus comprising:
a) a measurement chamber including m pieces of odor sensors having different responsive characteristics where m is an integer greater than one;
b) a gas introducer for introducing a sample gas into the measurement chamber;
c) a concentration adjuster for diluting or condensing the sample gas before introducing the sample gas into the measurement chamber;

d) a vector length computation unit for plotting, in a m-dimensional space formed by axes each corresponding to a detection signal generated by each of the m pieces of odor sensors, a measurement point representing a measurement result of the sample gas and for computing a vector length of an odor vector starting from an origin of the m-dimensional space and ending at the measurement point; and e) a controller for feedback-controlling the concentration adjuster so that the vector length computed by the vector length computation unit reaches a predetermined target value, wherein: the controller sets an allowance range across the target value and controls the gas introducer and the concentration adjuster so as to measure an odor of one sample gas at least two points in which the vector lengths of the odor vectors are shorter and longer than the target value within the allowance range; and the odor discriminating apparatus further comprises:

f) a measurement result computation unit for computing a measurement result at which the vector length is equal to the target value using a first measurement result and a second measurement result, the first measurement result being a result of measurement when the vector length is shorter than the target value within the allowance range and the second measurement result being a result of measurement when the vector length is longer than the target value within the allowance range, and for setting the computed measurement result as the measurement result of the sample gas, wherein: when the vector length of the odor vector is shorter than the target value within the allowance range, a condition of dilution or condensation by the concentration adjuster is fixed to a value at this point in time, measurements are repeated under a same condition, and a measurement value when a direction of the odor vectors is settled is set as the first measurement value; and when the vector length of the odor vector is longer than the target value within the allowance range, a condition of dilution or condensation by the concentration adjuster is fixed to a value at this point in time, measurements are repeated under a same condition, and a measurement value when a direction of the odor vectors is settled is set as the second measurement value.

* * * * *